United States Patent
Le Verger

(10) Patent No.: US 9,408,396 B2
(45) Date of Patent: Aug. 9, 2016

(54) TOTAL WEED CONTROL OF NON-AGRICULTURAL AREAS

(71) Applicant: OSMOBIO, Loudeac (FR)

(72) Inventor: Jacques Le Verger, Loudeac (FR)

(73) Assignee: OSMOBIO, Loudeac (FR)

( * ) Notice: Subject to any disclaimer, the term of this patent is extended or adjusted under 35 U.S.C. 154(b) by 0 days.

(21) Appl. No.: 14/380,363

(22) PCT Filed: Feb. 20, 2013

(86) PCT No.: PCT/FR2013/050350
§ 371 (c)(1),
(2) Date: Aug. 21, 2014

(87) PCT Pub. No.: WO2013/124583
PCT Pub. Date: Aug. 29, 2013

(65) Prior Publication Data
US 2015/0045222 A1    Feb. 12, 2015

(30) Foreign Application Priority Data

Feb. 23, 2012    (FR) ..................... 12 00525

(51) Int. Cl.
| | |
|---|---|
| *A01N 65/08* | (2009.01) |
| *A01N 43/90* | (2006.01) |
| *A01N 31/04* | (2006.01) |
| *A01N 65/28* | (2009.01) |
| *A01N 65/00* | (2009.01) |
| *A01N 31/02* | (2006.01) |
| *A01N 37/40* | (2006.01) |
| *A61K 36/185* | (2006.01) |

(52) U.S. Cl.
CPC ............... *A01N 65/08* (2013.01); *A01N 31/02* (2013.01); *A01N 31/04* (2013.01); *A01N 37/40* (2013.01); *A01N 43/90* (2013.01); *A01N 65/00* (2013.01); *A01N 65/28* (2013.01); *A61K 36/185* (2013.01)

(58) Field of Classification Search
CPC ....... A01N 65/00; A01N 31/02; A01N 31/04; A01N 43/90; A01N 65/28; A01N 2300/00; A01N 25/04; A01N 27/00; A01N 49/00; A01N 65/24; A01N 37/40; A01N 65/08
USPC ........................................................ 504/140
See application file for complete search history.

(56) References Cited

U.S. PATENT DOCUMENTS

| | | | |
|---|---|---|---|
| 5,998,335 | A | 12/1999 | Selga et al. |
| 2010/0016161 | A1* | 1/2010 | Richard et al. ............... 504/140 |
| 2010/0303940 | A1* | 12/2010 | Enan .......................... 424/778 |

FOREIGN PATENT DOCUMENTS

| | | |
|---|---|---|
| JP | 2010047489 A | 3/2010 |
| WO | 97/16975 A1 | 5/1997 |
| WO | 99/53764 A2 | 10/1999 |
| WO | 00/51436 A1 | 9/2000 |
| WO | 2006/094126 A2 | 9/2006 |

OTHER PUBLICATIONS

Kishore et al. (2002, International Arachis Newsletter 22:46-48).*
Vaughn et al., "Volatile monoterpenes as potential parent structures for new herbicides", Weed Science, Jan. 1, 1993, pp. 114-199, vo. 41, Weed Science Society of America, Champaign, IL, US.

* cited by examiner

*Primary Examiner* — Johann R Richter
*Assistant Examiner* — Courtney Brown
(74) *Attorney, Agent, or Firm* — IM IP Law PLLC; C. Andrew Im

(57) ABSTRACT

A herbicide composition for controlling weeds in non-agricultural areas. The composition comprises an aqueous infusion of the natural henna plant at a concentration of 14 to 18%, expressed in weight percent relative to the total weight of the composition, at least one non-ionic surfactant. The composition further comprises the following ingredients: 40 to 50% of at least one terpene oxide; 5 to 9% of at least one monoterpenol; and 4 to 8% of at least one monoterpene, such that the weight percentage of the solid natural henna used for the infusion is at least 2%.

9 Claims, No Drawings

TOTAL WEED CONTROL OF NON-AGRICULTURAL AREAS

RELATED APPLICATIONS

This application is a §371 application from PCT/FR2013/050350 filed Feb. 20, 2013, which claims priority from French Patent Application No. 12 00525 filed Feb. 23, 2012, each of which is herein incorporated by reference in its entirety.

TECHNICAL FIELD OF THE INVENTION

The present invention relates in particular to a composition intended for eradicating weeds in nonagricultural areas (NAA), usable diluted in water and applicable on the vegetation. This diluted composition is particularly suitable for treating plants during the period from March to November.

BACKGROUND OF THE INVENTION

The NAA that are particularly sensitive are those that line roads, and the companies tasked with road maintenance are constantly looking for effective solutions for ecological weed control. These companies are abandoning the use of conventional herbicides in favor of mechanical weeding such as mowing. Mowing is not, however, always easy to carrying out, depending on the configuration of the area to be treated, and the use of herbicides is still the only possible solution in many situations.

Herbicides are generally formulations that can be sprayed on the plants, most often causing contamination of the environment during application. Moreover, the herbicides obtained from synthetic chemistry are aggressive and cause destruction both of the root system of the plant, and of its airways.

To avoid this, the aim is to use products that allow targeted action and are not invasive (are not introduced into the whole plant by the roots via the sap), i.e. which are particularly effective on the plants to be eradicated, while remaining harmless to other living organisms.

To avoid the effects due most often to the use of toxic synthetic chemicals, it is possible to use herbicides based on natural products. In this context, for example a formulation of herbicide using various essential oils, such as oil from *Eucalyptus globulus*, is known from application JP2010047489. There is, however, a need to improve the specificity of the action of such herbicides and improve the efficacy for eradication of plants called "weeds".

OBJECT AND SUMMARY OF THE INVENTION

In this context and to overcome some or all of the drawbacks of the aforementioned prior art, according to a first aspect the present invention relates to a herbicide composition for total weed control of nonagricultural areas, containing an aqueous infusion of natural henna plant at a concentration from 14 to 18% expressed as percentage by weight relative to the total weight of the composition, at least one nonionic surfactant, and further comprising the following ingredients:

| | |
|---|---|
| at least one terpene oxide | 40 to 50% |
| at least one monoterpenol | 5 to 9% |
| at least one monoterpene | 4 to 8%; | and such that the weight of solid natural henna used for the infusion represents at least 2% of the total weight of the composition.

DETAILED DESCRIPTION OF THE EMBODIMENTS

In the context of the invention the term "terpene oxide" covers the terpenes, as they are defined conventionally in the nomenclature of organic compounds, comprising at least one ether oxide function.

Moreover, the term "monoterpene" denotes a compound so defined in the nomenclature of organic compounds excluding the monoterpenols and the term "monoterpenol" denotes a monoterpene comprising at least one alcohol function.

The three classes of compounds (terpene oxide, monoterpene and monoterpenol) will be designated with the general term "terpene derivatives".

The natural henna infusion is obtained from solid henna, which is infused for at least 5 minutes: 200 g of solid to 2 L of potable water heated to 70-80° C. (the volume of the infusion obtained is about 1.25 L).

The ingredients that make up the formulation according to the invention are herbicidal products that do not present long-lasting risks and have very little impact on health and the environment. In fact, the active substances and the additives in the composition according to the invention are entirely available from a raw material of vegetable, agricultural and renewable origin, and are moreover biodegradable completely, naturally and rapidly. Moreover, the ingredients in the ranges of values indicated are nontoxic in particular for humans and domestic animals.

The inventors discovered, quite unexpectedly, that the composition according to the invention, with the advantages listed above, is also particularly effective for eradicating weeds. This combination of various ingredients displays synergistic action that is selective and rapid on plants by destroying the chloroplasts of their respiratory system and their photosynthetic function. Moreover, the herbicide composition according to the invention is suitable for destroying the vascular system of unwanted plants and allows them to be eradicated at an early stage of their development.

The inventors discovered by chance that the terpene derivatives in the concentrations as presented above in the context of the invention and in combination with natural henna made it possible, owing to a synergistic effect, to destroy weeds. Natural henna contains polyphenols, for example derivatives of coumarin or of certain flavonoids. The inventors have shown that natural henna contains a significant amount of polyphenols, which is dissolved in the infusion. Moreover, the inventors have demonstrated that these polyphenols increase the efficacy of the terpene derivatives present in the composition for destroying weeds. Owing to this synergistic action between natural henna and these terpene derivatives, the composition according to the invention is particularly effective.

The flavonoids from the natural henna infusion perform two roles:
- they fix the monoterpenes on the surface of the treated plants and thus increase their herbicidal action over time; and
- they induce direct biochemical interactions by means of secondary metabolites that inhibit plant growth.

The inhibitory activity of the flavonoid compounds is due to their polyphenolic and isoprene-like molecular structure. Their molecules are in fact capable of playing a role in the oxidation-reduction chains to modify certain reactions relating to growth, respiration, and morphogenesis.

In addition, the composition offers the advantage of only targeting the undesirable species, and also gives a very wide spectrum of action, since it is for example capable of destroying both annual plants and perennial plants, hardy dicotyledons or also grasses.

Alternatively, the present invention relates to a herbicide composition for total weed control of nonagricultural areas, containing salicylic acid at a concentration from 6 to 20% expressed as percentage by weight relative to the total weight of the composition, at least one nonionic surfactant, and further comprising the following ingredients:

| | |
|---|---|
| at least one terpene oxide | 40 to 50% |
| at least one monoterpenol | 5 to 9% |
| at least one monoterpene | 4 to 8% |

The concentration of salicylic acid may advantageously be from 8 to 15%, or even from 9 to 12%. The nonionic surfactant may be selected from the sugar esters. The nature of the nonionic surfactant used is discussed in more detail later on in the text of the description, in the context of the present invention.

Preferably, the herbicide composition according to the invention comprises the following ingredients in the concentrations stated:

| | |
|---|---|
| at least one terpene oxide | 43.0 to 48.5% |
| at least one monoterpenol | 6.3 to 7.1% |
| at least one monoterpene | 5.5 to 6.2%. |

The herbicide composition according to the invention advantageously comprises 45.0 to 47.0% of terpene oxide, from 6.5 to 7.0% of monoterpenol and from 5.7 to 6.0% of monoterpene.

Preferably, the total weight of natural henna infused, i.e. used for the infusion, is less than 10%, advantageously less than 8%, and even more preferably less than 6% of the total weight of the composition. The inventors found, unexpectedly, that the substances infused from natural henna, in particular in these ranges of concentration, demonstrate synergistic action with the terpene derivatives for the herbicidal effect.

Preferably, the terpene oxide is 1,8-cineole; the monoterpenols are selected from linalool, terpinen-4-ol, alpha-terpineol and geraniol; and the monoterpenes are selected from alpha-pinene, beta-pinene, a terpinene such as gamma-terpinene, limonene, sabinene and para-cymene.

Preferably, the herbicide composition according to the present invention is prepared, in addition to the natural henna infusion, from at least three essential oils. It is prepared advantageously from the following three essential oils: essential oil of *Eucalyptus radiata*, advantageously 40 to 46%, essential oil of *Eucalyptus globulus*, advantageously 15 to 18%, and saro essential oil, advantageously 6 to 8 wt % relative to the total composition obtained. These oils make it possible to obtain compositions comprising the desired concentrations of terpene derivatives.

The composition according to the invention also advantageously comprises a preservative, preferably salicylic acid at a concentration from 10 to 30%. Alternatively (or in combination) salicylic acid is used at a concentration from 6 to 20%, preferably from 8 to 15%, and advantageously at a concentration from 9 to 12%.

Besides its role as a preservative, salicylic acid is a chemical mediator that helps to improve the systemic action of the composition according to the invention. The phenolic acids disturb the absorption of minerals by the plant: salicylic acid inhibits the absorption of $K^+$ ions in the roots. The degree of inhibition depends on the concentration of phenolic acid and on the pH. Decrease in pH leads to increased absorption of the phenolic compounds and therefore increased inhibition. This disturbance is due to the fact that the phenolic acids depolarize the membrane potential of the root cells, which alters membrane permeability and thus the rate of outflow of ions, both anions and cations. The extent of depolarization increases with increase in the concentration of phenolic acids. The inventors have shown that this effect is all the more surprising when salicylic acid is used.

The composition according to the invention comprises a nonionic surfactant. This nonionic surfactant is useful for solubilizing all the terpene substances or the oils in water; it is preferable to use a surfactant selected from the sugar esters (which are esters resulting from the condensation of sugars and fatty acids). Advantageously at least one polysorbate, at least one sorbitan ester and/or a capryl glucoside is used. These surfactants have the advantage that they are prepared from substances of natural origin, obtained from renewable and biodegradable resources.

The composition according to the invention also preferably comprises an emulsifying texture agent, which improves the adherence of the solution on the plants. Advantageously, the texture agent is gum arabic, preferably at a concentration from 3 to 15%, more preferably from 6 to 12%, or even 7 to 10%.

All the combinations of ranges of values given above in the context of the present invention are also possible. The composition is advantageously in the form of a sprayable solution, allowing the plants to be treated easily. When it contains an emulsifying texture agent, the solution according to the invention allows clean spraying, as this agent improves adherence of the sprayed solution on the vegetation: the solution is not immediately redistributed into the soil and it does not evaporate so readily.

According to another aspect, the present invention relates to the use of the composition as described above in the context of the present invention after dilution in water for eradicating weeds as a preventive or therapeutic measure. The dilution is preferably from 10 to 30%, and advantageously from 15 to 25% of the composition according to the invention made up with water to reach 100 wt %.

EXPERIMENTAL SECTION

1) Preparation of the Natural Henna Infusion 200 g of dry extract of natural henna in powder form is infused in 2 liters of water heated to 70-80° C. for 6 minutes. The solution is then left to return to room temperature, and then it is optionally filtered to remove the solid residues.

This gives 1.25 liters of useful infusion, which is able to keep its properties for 72 hours without preservatives at a temperature from 5 to 20° C. away from the light.

2) Chemical Composition of the Essential Oils

Tables 1, 2 and 3 present the chemical analysis of the terpenes carried out on the essential oils used for preparing the composition according to the invention.

These analyses are performed by chromatography:

Liquid chromatography (LC) for determining the organic compounds (the solvents and volatile compounds were determined by headspace gas chromatography).

TABLE 1

Essential oil of *Eucalyptus radiata*:

| terpene oxides | 1,8-cineole | 72.51% |
|---|---|---|
| monoterpenols | alpha-terpineol | 10.17% |
| 12.6% | terpinen-4-ol | 1.52% |
| | linalool | 0.45% |
| | geraniol | 0.46% |

TABLE 2

Essential oil of *Eucalyptus globulus*:

| terpene oxides | 1,8-cineole | 66.46% |
|---|---|---|
| monoterpenes | alpha-pinene | 15.89% |
| 20.39% | limonene | 2.10% |
| | beta-pinene | 0.47% |
| | para-cymene | 1.93% |

TABLE 3

Saro essential oil:

| terpene oxides | 1,8-cineole | 50.05% |
|---|---|---|
| monoterpenes | alpha-pinene | 5.12% |
| 28.22% | Sabinene | 8.18% |
| | beta-pinene | 8.02% |
| | Limonene | 4.27% |
| | gamma-terpinene | 2.63% |
| monoterpenols | terpinen-4-ol | 3.62% |
| 5.42% | Linalool | 0.70% |
| | alpha-terpineol | 1.10% |

3) Physicochemical Data for the Nonionic Surfactant

Description:

| Appearance | Liquid |
|---|---|
| Color | <3.0 VCS- clear, colorless to pale yellow |
| Dosage and application | non-ionic surfactant, solubilizer, ideal for cleaning formulas |
| Composition | non-ionic surfactant obtained from fatty alcohols and glucose of vegetable origin |

Technical Data:

| pH/PH: | (5.5 to 6.0) |
|---|---|
| Viscosity: | at 25° C.: 700-1100 mPa·s |
| Dry matter (%) | (58 to 62) |
| Preservative: | None |
| Closed-cup flash point, ° C. | >100 |
| Density | 1.150 g/cm³ at 20° C. |
| Solubility | Soluble in cold water |

Other nonionic surfactants usable in the herbicide composition, selected from the sugar esters: at least one polysorbate, at least one sorbitan ester and/or a capryl glucoside.

4) Preparation of the Herbicide Composition

Three compositions are prepared from the following ingredients, which are mixed in order to obtain the herbicide composition:

Composition 1
natural henna infusion 15-16%, salicylic acid 10-11%, nonionic surfactant (sugar ester) 7-8%, essential oil of *Eucalyptus radiata* 40-41%, essential oil of *Eucalyptus globulus* 15-16%, saro essential oil 6-7% and gum arabic 4%

Composition 2
The infusion differs from composition 1 only in the concentration of salicylic acid, which is 6-7% (it is made up with water to give 100%)

Composition 3
The infusion differs from composition 1 only in the concentration of salicylic acid, which is 0% (it is made up with water to give 100%)

5) Measurement of the Efficacy of the Composition According to the Invention Compared with Other Compositions Foliar applications are made based on the whole of the composition according to the invention described in section 4) of the present experimental section, which is diluted to 20 wt %. These applications were performed by spraying on dry vegetation throughout the season and in normal agricultural-climatic conditions:

temperatures between 14° C. and 22° C.;
hygrometry from 50% to 70%; and
in the absence of precipitation during the 3 h following the applications.

The plants treated are dicotyledons and thistles at different stages of development: rosette, seedling and in the growth phase.

The table given below shows the efficacy of the compositions according to the invention (1, 2 and 3; see section 4)) compared with control compositions (5, 6, 7, 8 and 9) that comprise the same concentrations by weight of nonionic surfactant (sugar ester), of essential oil of *Eucalyptus radiata*, of essential oil of *Eucalyptus globulus*, of saro essential oil and of gum arabic. Only the concentrations of natural henna and of salicylic acid were varied, making up with water if necessary to reach 100%:

| | 1 | 2 | 3 | 4 | 5 | 6 | 7 | 8 | 9 |
|---|---|---|---|---|---|---|---|---|---|
| Concentration of henna (in wt % before dilution to 20%) | 15 | 15 | 15 | 0 | 10 | 20 | 0 | 0 | 0 |
| Concentration of salicylic acid (in wt % before dilution to 20%) | 0 | 6 | 11 | 0 | 0 | 0 | 6 | 11 | 15 |
| Maximum rate of destruction of the plants | 40 | 80 | 100 | 20 | 30 | 40 | 40 | 60 | 60 |
| Time taken in days to reach the maximum rate of destruction of the plants | 12 | 16 | 16 | 12 | 16 | 12 | 16 | 12 | 12 |

Remarks:
For Composition 1, after 12 Days there is no Longer Any Change:
-> 40% of the dicotyledons are destroyed at the seedling stage.
-> the young shoots of thistles are destroyed whereas the developed thistles start growing actively again 15 days after application.

For Composition 2, at 12 Days there is Already 78% Destruction of the Plants:
-> 80% of the dicotyledons at the young and developed stage are destroyed.
-> Grasses: rye-grass—annual meadow grass—fescues at the young stage are destroyed to 75%.
-> Young thistles are destroyed; the leaf system of the thistles is destroyed to 90% during the 10 days following application.
For Composition 3, at 12 Days there is Already 95% Destruction of the Plants:
-> The dicotyledons at the seedling and developed stage are destroyed to 100%.
-> Grasses in the growth phase are destroyed to 100%.
-> Thistles in the growth phase and flowering are destroyed to 100%.
For Composition 4:
-> Only 20% of the dicotyledons are destroyed at the seedling stage.
-> All the thistles, whatever their vegetative stage, are resistant and start growing actively again 15 days after application.
For Composition 5:
-> 30% of the dicotyledons are destroyed at the seedling stage.
-> The young shoots of thistles are destroyed whereas the developed thistles start growing actively again 15 days after application.
For Composition 6:
-> 40% of the dicotyledons are destroyed at the seedling stage.
-> The young shoots of thistles are destroyed whereas the developed thistles start growing actively again 15 days after application.
For Composition 7:
-> 40% of the dicotyledons are destroyed at the seedling stage.
-> Young thistles are destroyed; the leaf system of the thistles is destroyed to 80% during the 10 days following application.
For Composition 8:
-> 60% of the dicotyledons are destroyed at the seedling stage.
-> Young thistles are destroyed; the leaf system of the thistles is destroyed to 80% during the 10 days following application.
For Composition 9:
-> 60% of the dicotyledons are destroyed at the seedling stage.
-> Young thistles are destroyed; the leaf system of the thistles is destroyed to 80% during the 10 days following application.

CONCLUSIONS

Using monoterpene alone provides a rate of destruction of 20%.

Exclusive incorporation of henna extracts at 10% concentration makes it possible to obtain a level of efficacy of 30% whereas when incorporated at 15%, the rate of destruction is 40%, or an improvement in herbicidal efficacy of 10%. When incorporated at 20%, the results are identical to the 15% concentration.

Exclusive incorporation of salicylic acid at 6% concentration makes it possible to obtain a level of efficacy of 40% whereas when incorporated at 11%, the degree of destruction is 60%, or an improvement in herbicidal efficacy of 20%. Increasing the level of salicylic acid from 11% to 15% is not justified: the optimal concentration of salicylic acid in the concentrated formula is 11%.

It is thus found that increasing the concentrations of henna or of salicylic acid, when one is used without the other in the composition, does not give degrees of destruction above 60%.

Incorporation of henna extracts at 15% and salicylic acid at 6% makes it possible to obtain an efficacy of 80% for the dicotyledons and 75% for grasses.

Incorporation of henna extracts at 15% and salicylic acid at 11% makes it possible to obtain an efficacy of 100%. All of the plants are destroyed.

There is clearly a synergistic effect of the henna/salicylic acid combination in the presence of the terpene derivatives as described above.

The invention claimed is:

1. A herbicide composition for controlling weeds in non-agricultural areas, comprising an aqueous infusion of a natural henna plant at a concentration from 14 to 18%; at least one nonionic surfactant; 40 to 50% of at least one terpene oxide; 5 to 9% of at least one monoterpenol; 4 to 8% of at least one monoterpene; and wherein a weight of a solid natural henna used for the aqueous infusion represents at least 2%, the percentages expressed are by weight relative to a total weight of the composition.

2. The composition as claimed in claim 1, further comprising the following ingredients in concentrations stated: 43.0 to 48.5% of at least one terpene oxide; 6.4 to 7.1% of at least one monoterpenol; and 5.5 to 6.2% of at least one monoterpene.

3. The composition as claimed in claim 1, wherein the terpene oxide is 1,8-cineole; the monoterpenols are selected from linalool, terpinen-4-ol, alpha-terpineol and geraniol; and the monoterpenes are selected from alpha-pinene, beta-pinene, a terpinene such as gamma-terpinene, limonene, sabinene and para-cymene.

4. The composition as claimed in claim 1 is prepared, in addition to the natural henna infusion, from an essential oil of *Eucalyptus radiata*, an essential oil of *Eucalyptus globulus*, and a saro essential oil.

5. The composition as claimed in claim 1, further comprising 10 to 30% of salicylic acid.

6. The composition as claimed in claim 1, wherein the nonionic surfactant is selected from sugar esters.

7. The composition as claimed in claim 1, further comprising an emulsifying texture agent.

8. The composition as claim in claim 7, wherein the emulsifying texture agent is a gum arabic.

9. Method of eradicating weed in non-agricultural area, comprising the steps of:
diluting a herbicide composition in water, the herbicide composition comprising an aqueous infusion of a natural henna plant at a concentration from 14 to 18%; at least one nonionic surfactant; 40 to 50% of at least one terpene oxide; 5 to 9% of at least one monoterpenol; 4 to 8% of at least one monoterpene; and wherein a weight of a solid natural henna used for the aqueous infusion represents at least 2%, the percentages expressed are by weight relative to a total weight of the composition; and
applying the diluted herbicide composition in said non-agricultural area to eradicate weeds as a preventive or therapeutic measure.

* * * * *